(12) United States Patent
Ishii

(10) Patent No.: US 8,594,273 B2
(45) Date of Patent: Nov. 26, 2013

(54) CT SCANNING TABLETOP AND X-RAY CT APPARATUS

(75) Inventor: Takahiro Ishii, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 390 days.

(21) Appl. No.: 13/021,246

(22) Filed: Feb. 4, 2011

(65) Prior Publication Data

US 2011/0188627 A1    Aug. 4, 2011

(30) Foreign Application Priority Data

Feb. 4, 2010 (JP) ................................. P2010-23326

(51) Int. Cl.
*A61B 6/04* (2006.01)
*H05G 1/02* (2006.01)

(52) U.S. Cl.
USPC ............................................ 378/20; 378/209

(58) Field of Classification Search
USPC ............ 378/4–20, 204, 208–210; 5/600, 601, 5/612, 613, 617, 618, 621–624
See application file for complete search history.

(56) References Cited

U.S. PATENT DOCUMENTS

| | | | |
|---|---|---|---|
| 4,989,849 A * | 2/1991 | Zupancic et al. ................. 5/622 |
| 5,097,132 A * | 3/1992 | Plummer .................. 250/363.08 |
| 5,771,512 A * | 6/1998 | Kurakake et al. .................. 5/623 |
| 7,263,733 B2 * | 9/2007 | Fujita et al. ........................ 5/601 |
| 2005/0059877 A1 * | 3/2005 | Falbo ............................ 600/407 |

FOREIGN PATENT DOCUMENTS

| | | |
|---|---|---|
| CN | 1415272 A | 5/2003 |
| JP | 8-299325 | 11/1996 |
| JP | 2003-135446 A | 5/2003 |

OTHER PUBLICATIONS

Chinese Office Action Issued Jul. 2, 2012 in Patent Application No. 201110035146.6 (with English translation).
Office Action issued Mar. 22, 2013, in Chinese Patent Application No. 201110035146.6 (with English-language translation).

* cited by examiner

*Primary Examiner* — Anastasia Midkiff
(74) *Attorney, Agent, or Firm* — Oblon, Spivak, McClelland, Maier & Neustadt, L.L.P.

(57) ABSTRACT

According to one embodiment, a CT scanning tabletop includes a tabletop body and an aid. The tabletop body has a placement surface where a subject is to be placed, and is formed in a manner that an X-ray transmission loss by one end portion in a longitudinal direction thereof is smaller than an X-ray transmission loss by a portion of the tabletop body other than the one end portion. The aid is provided on the one end portion in a manner that the aid is attachable and detachable by moving in advancing and retreating directions toward and away from the placement surface, the aid is configured to hold a part of the subject.

17 Claims, 5 Drawing Sheets

US 8,594,273 B2

CT SCANNING TABLETOP AND X-RAY CT APPARATUS

CROSS-REFERENCE TO THE RELATED APPLICATION

This application is based upon and claims the benefit of priority from Japanese Patent Application No. 2010-23326, filed on Feb. 4, 2010; the entire contents of which are incorporated herein by reference.

FIELD

The embodiments relate to a CT scanning tabletop and an X-ray CT apparatus. The embodiments relate to a CT scanning tabletop and an X-ray CT apparatus which include an aid for holding a part of a subject, for example.

BACKGROUND

An X-ray CT apparatus irradiates a subject with X-rays generated by an X-ray tube, detects X-rays transmitted through the subject, and provides image data on the subject generated on the basis of the detection signal. Such X-ray CT apparatuses play an important role in medical practices such as diagnosis and treatment. The X-ray CT apparatus includes a gantry having an X-ray irradiator that irradiates a subject placed on a tabletop with X-rays and an X-ray detector that detects X-rays transmitted through the subject. The gantry has a cylindrical opening. The tabletop is moved to transfer the subject into the opening. Then, while rotating around the subject, the X-ray irradiator including an X-ray tube irradiates the subject with X rays and the X-ray detector detects X-rays transmitted through the subject. In this way, the CT scanning of the subject is performed.

In this regard, there is known an aid for holding a part of a subject placed on a tabletop in CT scanning, such as a headrest for holding the head and an armrest for holding the arm.

The aid has connecting portions, and the tabletop has connection holes provided in an edge portion on the gantry side and arranged along a longitudinal direction of the tabletop. The aid is moved from one side of the tabletop to the longitudinal edge portion on the gantry side and is fixed to the tabletop by inserting the connecting portions into the connection holes. When the scanning is completed, the tabletop with the aid fixed thereto is lowered to a height that is lower than the opening of the gantry and that makes it easy for the subject to get on and off the tabletop (hereinafter, boarding height). After the subject gets off the tabletop, the aid is replaced with an aid suitable for a scanning part of the next subject as necessary.

Meanwhile, generally there is not a sufficient space between the gantry and the edge portion of the tabletop on the gantry side. For this reason, when the tabletop stays at the boarding height lower than the opening of the gantry, the gantry positioned close to the tabletop hinders the aid from being moved in a direction opposite to the direction in which the aid is inserted. Consequently, the aid cannot be removed. Thus, after completion of the scanning, in a case where the aid needs to be removed from the tabletop, or where an aid needs to be attached to the tabletop for the next scanning, the tabletop has to be raised to such a height around the opening that any hindrance can be avoided. Then, after the aid is attached or detached, the tabletop has to be lowered again to the boarding height. This brings about a problem that operations to move the tabletop vertically are needed and require a lot of work.

DETAILED DESCRIPTION

According to one embodiment, a CT scanning tabletop includes a tabletop body and an aid. The tabletop body has a placement surface where a subject is to be placed, and is formed in a manner that an X-ray transmission loss by one end portion in a longitudinal direction thereof is smaller than an X-ray transmission loss by a portion of the tabletop body other than the one end portion. The aid is configured to hold a part of the subject, and is provided on the one end portion in a manner that the aid is attachable and detachable by moving in advancing and retreating directions toward and away from the placement surface.

Various Embodiments will be described hereinafter with reference to the accompanying drawings.

First Embodiment

A first embodiment will be described with reference to FIGS. 1 to 6.

Figure 1:
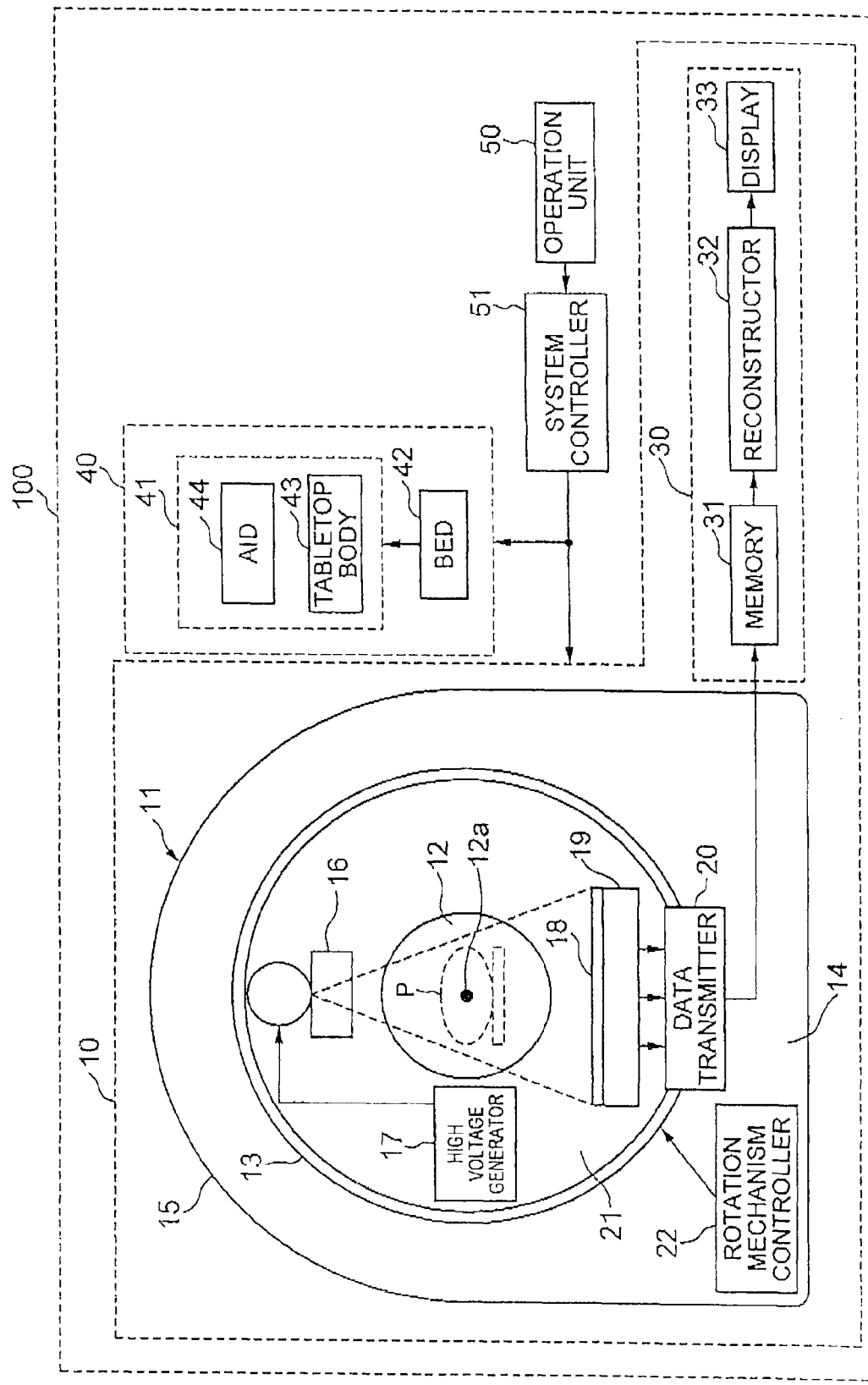
FIG. 1 is a block diagram showing the configuration of an X-ray CT apparatus according to a first embodiment.

FIG. 1 is a block diagram showing the configuration of an X-ray CT apparatus according to the first embodiment. The X-ray CT apparatus 100 includes: a scanner 10 for CT scanning a subject P; a bed unit 40 for moving the subject P toward the scanner 10; an operation unit 50 for providing inputs to operate the scanner 10 and the bed unit 40; and a system controller 51 for controlling the scanner 10 and the bed unit 40 on the basis of the input information from the operation unit 50.

The scanner 10 includes: a gantry 11 for creating projection data through the CT scanning on the subject P; and an image processor 30 for creating image data by processing the projection data created by the gantry 11.

The gantry 11 includes: a cylindrical opening 12 into which the subject P is transferred by the bed unit 40; a rotator 13 which rotates about a CT imager center 12a around the subject P transferred in the opening 12; a fixer 14 which supports the rotator 13 rotatably; and a cover 15 which covers the rotator 13 and the fixer 14.

The rotator 13 includes: an X-ray irradiator 16 disposed outside the circumference of the opening 12 for X-ray irradiation; a high voltage generator 17 for supplying a high voltage to the X-ray irradiator 16; an X-ray detector 18 for detecting X-rays; a data collector 19 for collecting detection signals detected by the X-ray detector 18 and generating projection data; a transmitting portion of a data transmitter 20 for outputting the projection data created by the data collector 19 to the image processor 30; and a rotation frame 21 for rotatably supporting the X-ray irradiator 16, the high voltage generator 17, the X-ray detector 18, the data collector 19, and the transmitting portion of the data transmitter 20.

The X-ray irradiator 16 has an X-ray tube, and generates X-rays using the high voltage supplied from the high voltage generator 17. The X-ray irradiator 16 irradiates the subject P transferred into the opening 12 with the X-rays, while rotating. The X-ray detector 18 has an X-ray detection element, and is disposed opposite to the X-ray irradiator 16. The X-ray detector 18 detects X-rays transmitted through the subject P, the X-rays being irradiated from the X-ray irradiator 16. The X-ray detector 18 then coverts the result into an electrical signal, amplifies the converted signal, and outputs the signal to the data collector 19.

The data collector 19 includes an analog-to-digital converter (ADC) and so forth, and converts an analog signal, which is outputted from the X-ray detector 18, to a digital signal. Then, the data collector 19 collects the digital signal obtained at each predetermined rotation angle of the rotation frame 21, and creates projection data for one view.

The data transmitter 20 includes the transmitting portion and a receiving portion for transmission and reception by use of light, for example. The transmitting portion is provided at the rotator 13, and projection data from the data collector 19 is transmitted to the receiving portion provided at the fixer 14.

The fixer 14 includes: a rotation mechanism controller 22 for rotating the rotation frame 21 of the rotator 13; and the receiving portion of the data transmitter 20. The rotation mechanism controller 22 includes a rotation mechanism for rotating the rotation frame 21 and a control circuit for controlling the rotation mechanism. Moreover, the receiving portion of the data transmitter 20 outputs projection data, which is transmitted from the transmitting portion, to the image processor 30.

The image processor 30 includes: a memory 31 for storing the projection data outputted from the data transmitter 20 at the rotator 13 in the gantry 11; a reconstructor 32 for reconstructing pieces of projection data for multiple views stored in the memory 31 to create image data; and a display 33 for displaying the image data created by the reconstructor 32.

The bed unit 40 includes: a tabletop 41 on which the subject P is placed, and which is disposed close to the gantry 11; and a bed 42 which supports the tabletop 41 movably in a vertical direction and in a longitudinal direction thereof. The tabletop 41 includes: a plate-shaped rectangular tabletop body 43 on which the subject P is placed; and an aid 44 which holds a part of the subject P placed on the tabletop body 43.

The bed 42 has: a longitudinal movement mechanism for moving the tabletop 41 in the longitudinal direction to transfer the subject P into the opening 12 of the gantry 11; and a vertical movement mechanism for moving the tabletop 41 in the vertical direction in order for the subject P to get on or off the tabletop 41. To perform scanning when the subject P is transferred into the opening 12 from the head side, the tabletop 41 is moved into the opening 12 in such a way that the subject P placed in a lying posture on the tabletop 41 has the head directed toward one end portion of the tabletop 41 and the legs directed toward an opposite end portion thereof. In contrast to the above, to perform scanning when the subject P is transferred into the opening from the leg side, the tabletop 41 is moved into the opening 12 in such a way that the subject P placed in a lying posture on the tabletop 41 has the legs directed toward the one end portion of the tabletop 41 and the head directed toward the opposite end portion thereof.

The operation unit 50 is an interactive interface including input devices such as a keyboard, a trackball, a joystick, and a mouse, a display panel, in addition to various switches and the like. The operation unit 50 is for various input operations with regard to the CT scanning on the subject P, such as operations to move the tabletop 41 of the bed unit 40.

The system controller 51 includes a CPU and a memory circuit. Once storing the input information supplied from the operation unit 50 by the input operation, the system controller 51 then performs controls over the entire system on the basis of the input information, such as controls on rotation of the rotation frame 21 of the rotator 13 in the gantry 11 of the scanner 10, creation of projection data, creation of image data, display, and movement of the tabletop 41 of the bed unit 40.

Figure 2:
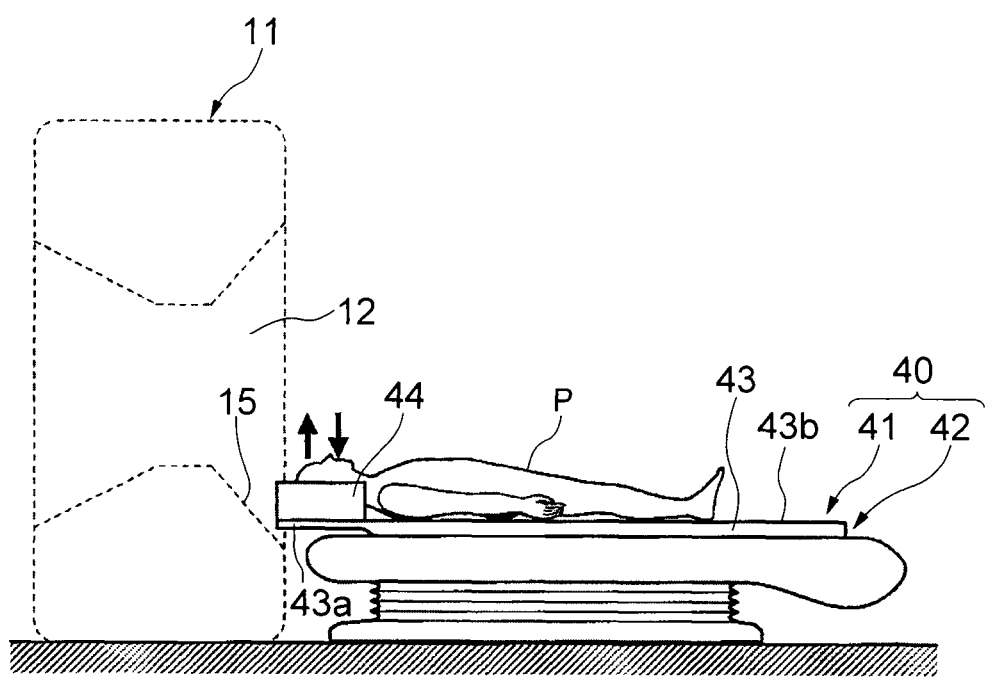
FIG. 2 is a view showing details of the configuration of a tabletop body of a tabletop according to the first embodiment.
Figure 3:
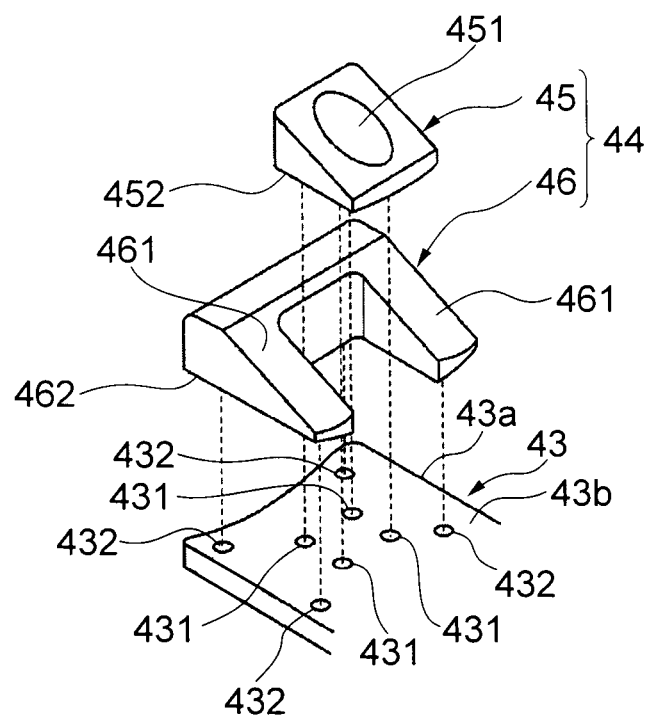
FIG. 3 is a view showing details of the configuration of an aid for the tabletop according to the first embodiment.
Figure 4:
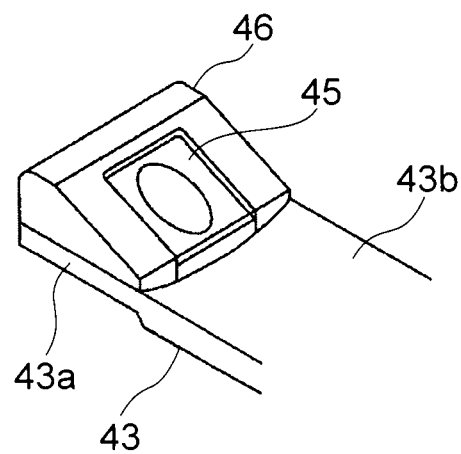
FIG. 4 is a view showing the aid provided on the tabletop body according to the first embodiment.

Next, details of the configuration of the tabletop 41 of the bed unit 40 will be described with reference to FIGS. 1 to 4. FIG. 2 is a view showing details of the configuration of the tabletop body 43 of the tabletop 41. FIG. 3 is a view showing details of the configuration of the aid 44 for the tabletop 41. FIG. 4 is a view showing the aid 44 provided on the tabletop body 43.

In FIG. 2, before CT scanning is started, the tabletop 41 stays at a boarding height as a home position where it is easy for the subject P to get on and off the tabletop 41, the position being close to the gantry 11 of the scanner 10. At the time of CT scanning, the tabletop 41 is moved upward, and then moved into the opening 12 of the gantry 11 from the side of the one end portion in the longitudinal direction.

The tabletop body 43 is made of, for example, a carbon composite material having a high strength and a high X-ray transmittance. Moreover, the tabletop body 43 is formed to have a length, in the longitudinal direction of the tabletop body 43, that allows the opposite end portion to be supported by the bed 42 at a position where the tabletop body 43 is extended toward the gantry 11 to the maximum in order to allow scanning of the entire body of the subject P. Moreover, a portion of the tabletop body 43 which is other than one end portion 43a in the longitudinal direction, and which supports most of the weight of the subject P, is formed to have a thickness in the vertical direction large enough not to be bent due to the weight of the subject P, but small enough to minimize an unnecessary X-ray transmission loss except for an X-ray transmission loss by the subject P.

Furthermore, the aid 44 is provided on the one end portion 43a in the longitudinal direction, the one end portion 43a supporting a part of the weight of the subject P. Thus, the thickness in the vertical direction of the one end portion 43a is formed to be such a thickness that the one end portion 43a and the aid 44 provided on the one end portion 43a may only cause an unnecessary X-ray transmission loss, except for an X-ray transmission loss by the subject P, nearly as small as the loss by the portion other than the one end portion 43a. In other words, the one end portion 43a is formed to have a smaller thickness than the portion other than the one end portion 43a; the difference in thickness corresponds to the amount of X-rays absorbed by the aid 44. In addition, as shown in FIG. 3, on a placement surface on the one end portion 43a within the area of a placement surface 43b where the subject P is placed, multiple recesses 431, 432 matching with the aid 44 are provided. As an example of the recesses 431, 432, holes are used.

FIG. 3 is the view showing the details of the configuration of the aid 44. The aid 44 includes a headrest 45, an armrest 46, and the like, which are made of, for example, a carbon composite material having a high rigidity and a high X-ray transmittance. Each component of the aid 44 is individually provided on the one end portion 43a of the tabletop body 43 and is attachable and detachable by moving in advancing and retreating directions, for example, the vertical direction, toward and away from the placement surface 43b of the tabletop body 43 where the subject P is placed.

The headrest 45 includes: a top surface 451 formed into a curved surface fitted to the shape of the back of the head of the subject P; a bottom surface 452 formed into a surface fitted to the shape of a top surface of the tabletop body 43 on which the headrest 45 is disposed; and unillustrated protrusions provided to the bottom surface 452 and respectively engageable with the recesses 431 for fixing the position of the headrest 45 to the tabletop body 43.

When CT scanning is performed on the head of the subject P, the headrest 45 is provided approximately at the center in a width direction of the tabletop body 43 and holds the head of the subject P placed in a lying posture on the tabletop body 43. This prevents the body of the subject P from moving during the CT scanning.

The armrest 46 includes: two top surfaces 461 respectively formed into curved surfaces tilted and fitted to the shape of the two arms of the subject P; a bottom surface 462 formed into a surface fitted to the shape of the top surface of the tabletop body 43 on which the armrest 46 is disposed; and unillustrated protrusions provided to the bottom surface 462 and respectively engageable with the recesses 432 for fixing the position of the armrest 46 to the tabletop body 43.

When CT scanning is performed on the trunk such as the lung and the abdomen of the subject P, as shown in FIG. 4, the armrest 46 is provided at a position adjacent to, and along both sides of, the headrest 45 provided on the tabletop body 43. The armrest 46 holding the arms near the head of the subject P placed in a lying posture on the tabletop body 43. This prevents the arms of the subject P from blocking the CT scanning on the chest. Moreover, when CT scanning is performed on the head of the subject P, the armrest 46 provided on the tabletop body 43 blocks the CT scanning on the head of the subject P. For this reason, the armrest 46 is removed from the tabletop body 43.

The armrest 46 is moved in the vertical direction toward the one end portion 43a of the tabletop body 43 as described above. This makes it possible to avoid a hindrance by the headrest 45 provided on the tabletop body 43. Additionally, the armrest 46 is easily detached and attached solely.

Incidentally, an attachable and detachable foot mat can be provided on the tabletop body 43. The foot mat includes: a top surface formed into a curved surface fitted to the shape of the legs of the subject P; a bottom surface formed into a surface fitted to the shape of the top surface of the tabletop body 43 on which the foot mat is disposed; and protrusions provided to the bottom surface and engageable with the recesses 432 for fixing the position of the foot mat to the tabletop body 43. The foot mat is attached when FF scanning is performed after the subject P is transferred into the opening 12 of the gantry 11 from the leg side. In this case, the foot mat holds the legs of the subject P placed in a lying posture on the tabletop body 43.

The aid 44 is provided on the one end portion 43a of the tabletop body 43 formed to have a small thickness as described above. This makes it possible to mitigate an X-ray transmission loss by the aid 44 when the CT scanning is performed. Furthermore, by moving in the vertical direction, the aid 44 are attached and detached without having a hindrance by the gantry 11. Accordingly, the aid 44 can be attached and detached regardless of the height of the tabletop 41.

In a case where the recesses 431, 432 on the tabletop body 43 block CT scanning and may cause an artifact, the following configurations may be adopted in place of the configuration of the recesses 431, 432 and the protrusions of the armrest 44 and the headrest 45 engageable with these recesses. Specifically, notches are provided on a region outside the image data region of the subject P, for example, provided in the vertical direction on an edge surface on the one end portion 43a in the longitudinal direction of the tabletop body 43; additionally, the bottom surface 462 of the armrest 46 are provided with protrusions detachably engageable with the notches on the tabletop body 43 by moving in the vertical direction. Alternatively, notches are provided in the vertical direction on a central portion of a side surface of the armrest 46 surrounding the headrest 45 in three directions; additionally, the headrest 45 are provided with protrusions engageable with the notches on the armrest 46 that is attachable and detachable by moving in the vertical direction.

Figure 5:
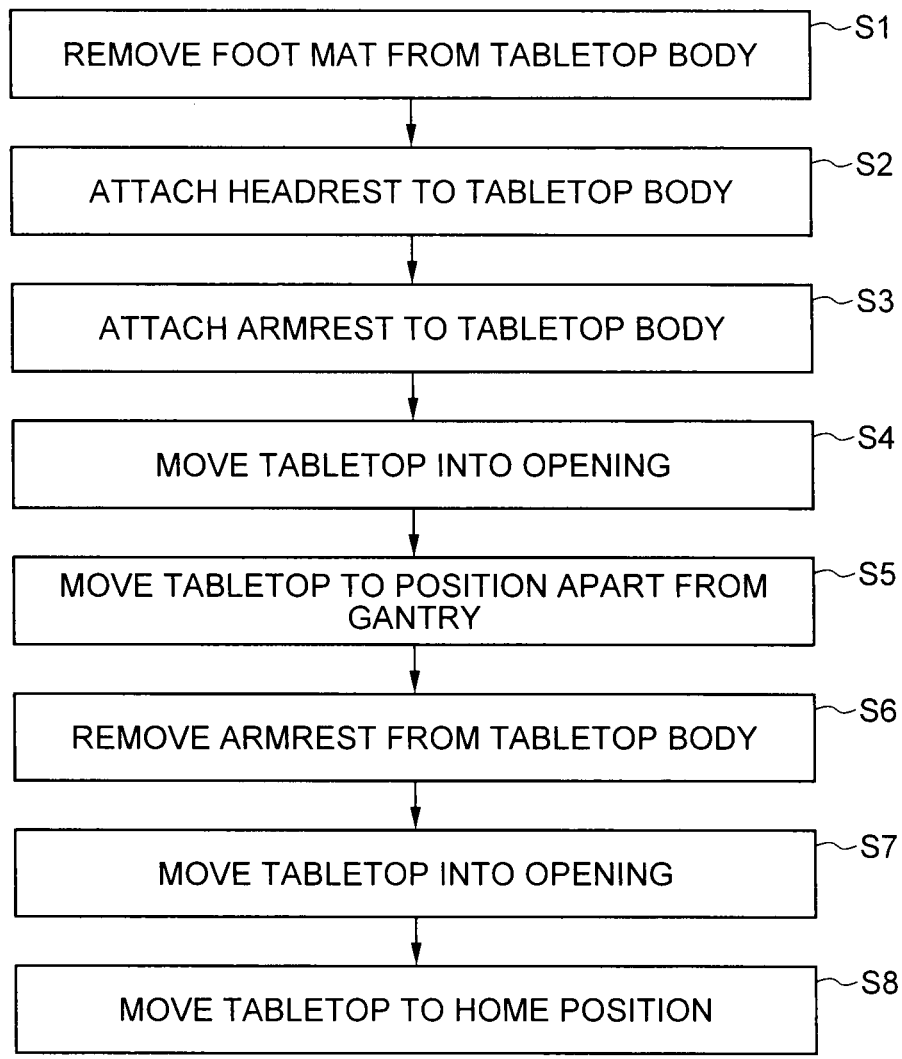
FIG. 5 is a flowchart for illustrating the procedure of CT scanning operations using the tabletop according to the first embodiment.
Figure 6:
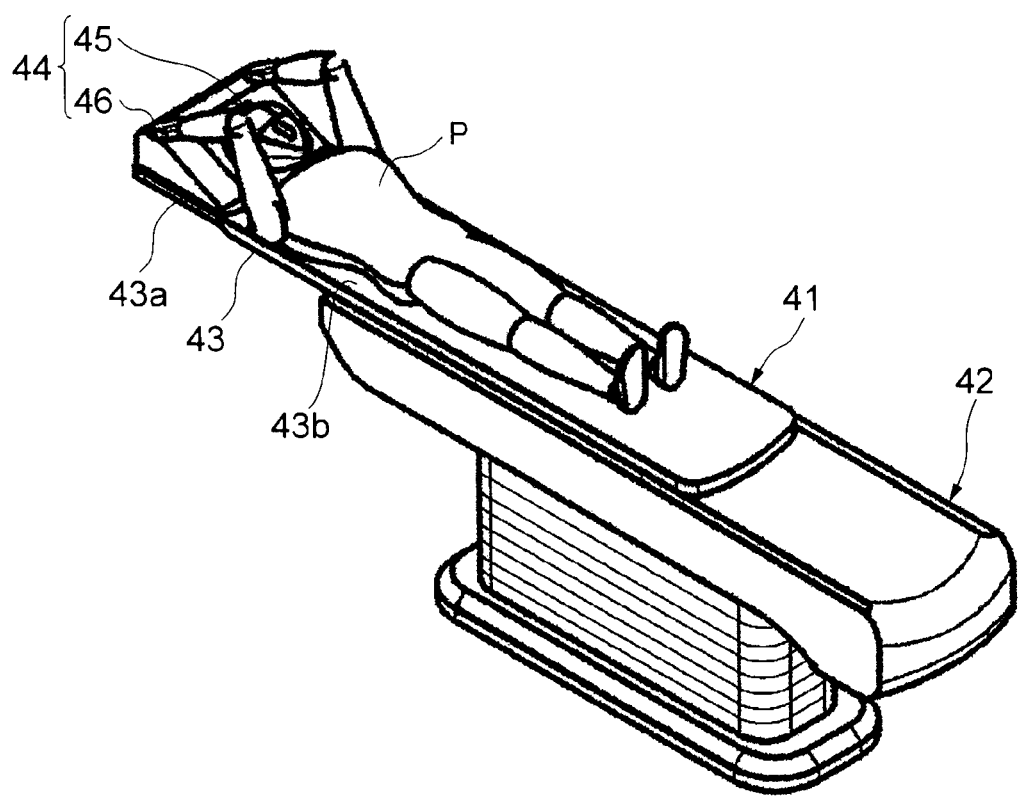
FIG. 6 is a view showing a state where a subject is placed in a lying posture on the tabletop body according to the first embodiment with the head being held by a headrest and the arms being held by an armrest.

Hereinafter, CT scanning operations using the tabletop 41 will be described with reference to FIGS. 1 to 6. FIG. 5 is a flowchart for illustrating the procedure of the CT scanning operations using the tabletop 41. FIG. 6 is a view showing a state where the subject P is placed in a lying posture on the tabletop body 43 with the head held by the headrest 45 and the arms held by the armrest 46.

In FIG. 5, after completion of CT scanning, the tabletop 41 of the bed unit 40 is moved to a retreating position. For example, the foot mat is provided on the one end portion 43a of the tabletop body 43.

To perform CT scanning on, for example, the head, the lung, and the abdomen of subject P, the operator of the X-ray CT apparatus 100 first moves the foot mat of the tabletop body 43 upward to remove the foot mat from the tabletop body 43 (Step S1).

Next, the headrest 45 is moved downward from the above of the one end portion 43a of the tabletop body 43 to engage the protrusions of the headrest 45 with the recesses 431. Thereby, the headrest 45 is attached to the tabletop body 43 (Step S2).

In this manner, even when the tabletop 41 stays at the home position, the attachment of the headrest 45 can be performed, regardless of the height of the tabletop 41, by moving the headrest 45 downward from the above of the one end portion 43a of the tabletop body 43. Thus, the work and the operation time for attaching and detaching the aid 44 such as operations to move the tabletop 41 upward and downward can be reduced.

Moreover, the armrest 46 is moved downward from the above of the one end portion 43a of the tabletop body 43 to engage the protrusions of the armrest 46 with the recesses 432. Thereby, the armrest 46 is attached to the tabletop body 43 (Step S3).

Then, after the subject P is lifted on the tabletop 41, to perform CT scanning on the lung and the abdomen of the subject P, the tabletop 41 is moved into the opening 12 by an operation through the operation unit 50, while the subject P is placed in a lying posture on the tabletop body 43 with the head held by the headrest 45 and the arms held by the armrest 46 as shown in FIG. 6 (Step S4).

After the completion of the CT scanning on the lung and the abdomen of subject P, by an operation through the operation unit 50, the tabletop 41 is moved to a position apart from the gantry 11 in the longitudinal direction (Step S5).

After the movement of the tabletop 41, the arms of the subject P held by the armrest 46 are put at the sides of the body. Next, to prevent the head of the subject P from blocking the CT scanning, the armrest 46 is moved upward and removed from the tabletop body 43 (Step S6).

With the head of the subject P held by the headrest 45, by moving the armrest 46 upward in the aforementioned manner, the removal of the armrest 46 from the tabletop body 43 is possible. Accordingly, the armrest 46 can be removed without raising the upper half of the subject P on the tabletop body 43. Thus, the burden to the subject P can be reduced. Furthermore, in a case of scanning using a contrast agent, the burden to the operator who has a short scanning time can be reduced.

Incidentally, after CT scanning is performed on the head, the lung and the abdomen may be scanned. In this case, first the headrest 45 is attached to the tabletop body 43, and the head of the subject P is scanned. Then, while the head of the subject P is being held by the headrest 45, the armrest 46 is moved downward from the above of the one end portion 43a of the tabletop body 43 and attached to the tabletop body 43. Accordingly, the armrest 46 can be removed without raising the upper half of the subject P on the tabletop body 43. Thus, the burden to the subject P can be reduced.

After the armrest 46 is removed, to perform CT scanning on the head of the subject P, the tabletop 41 is moved into the opening 12 by an operation through the operation unit 50 (Step S7).

In this CT scanning, the X-ray irradiator 16 in the gantry 11 irradiates the subject P with X-rays. The X-ray detector 18 detects X-rays transmitted through the head of the subject P, the headrest 45, and the one end portion 43a of the tabletop body 43. The data collector 19 creates projection data on the basis of detection signals from the X-ray detector 18. The image processor 30 creates and displays image data on the basis of multiple pieces of projection data created by the data collector 19.

As described above, the aid 44 is provided on the one end portion 43a that is a thinned portion of the tabletop body 43. This makes it possible to make the X-ray transmission loss by the one end portion 43a and the aid 44 nearly as small as the loss by the portion other than the one end portion 43a.

After the completion of the CT scanning on the head of subject P, by an operation through the operation unit 50, the tabletop 41 is moved to the home position (Step S8).

As has been described above, according to the first embodiment, the tabletop body 43 on which the subject P is placed is formed in a manner that the X-ray transmission loss by the one end portion 43a is smaller than the X-ray transmission loss by the portion other than the one end portion 43a. To put it differently, the thickness of the one end portion 43a of the tabletop body 43 on which the subject P is placed is formed smaller than the thickness of the portion other than the one end portion 43a. The aid 44 is provided on the one end portion 43a that is formed thin. This makes it possible to make the X-ray transmission loss by the one end portion 43a and the aid 44 as small as the loss by the portion other than the one end portion 43a.

Moreover, the aid 44 attachable and detachable by moving in the vertical direction is provided on the one end portion 43a of the tabletop body 43. Thereby, the aid 44 can be attached and detached regardless of the height of the tabletop 41. Thus, the work and the operation time for attaching and detaching the aid 44 can be reduced.

Furthermore, while the subject P is placed in a lying posture on the tabletop body 43 with the head held by the headrest 45, by moving the armrest 46 in the vertical direction, the attachment and detachment of the armrest 46 are possible. Thus, the burden to the subject P can be reduced.

Second Embodiment

Figure 7:
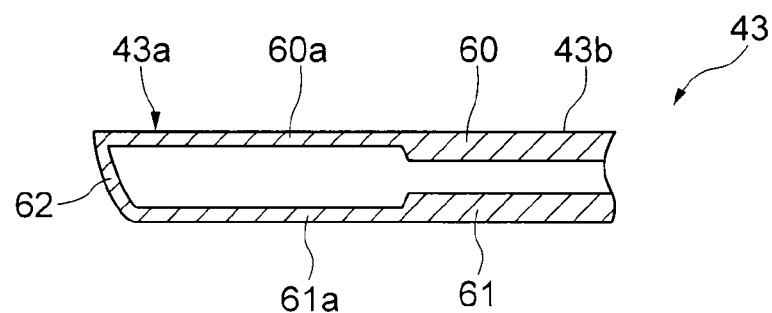
FIG. 7 is a cross-sectional view showing details of the configuration of a tabletop body of a tabletop according to a second embodiment.

A second embodiment of the present invention will be described with reference to FIG. 7. FIG. 7 is a cross-sectional view showing details of the configuration of a tabletop body 43 of a tabletop 41.

The second embodiment of the present invention is basically the same as the first embodiment. In the second embodiment, the difference from the first embodiment will be described. Portions that are the same as the portions described in the first embodiment are denoted by the same reference numerals, and descriptions thereof will be omitted.

As shown in FIG. 7, in the second embodiment of the present invention, the tabletop body 43 includes: a plate-shaped first wall portion 60 having the placement surface 43b where the subject P is placed; a plate-shaped second wall portion 61 facing the first wall portion 60 at a distance; and a side wall portion 62 connecting the periphery of the first wall portion 60 to the periphery of the second wall portion 61. Specifically, a cavity is formed inside the tabletop body 43, and the interior space is filled with air.

The first wall portion 60 is formed in a manner that a first one end portion 60a has a smaller thickness in a longitudinal direction thereof than a portion other than the first one end portion 60a. Furthermore, the second wall portion 61 is also formed in a manner that a second one end portion 61a in a longitudinal direction thereof (specifically, the second one end portion 61a facing the first one end portion 60a of the first wall portion 60) has a smaller thickness than a portion other than the second one end portion 61a. Accordingly, the one end portion 43a of the tabletop body 43 includes the first one end portion 60a and the second one end portion 61a facing the first one end portion 60a at a distance. The side wall portion 62 is formed as a side wall connecting the periphery of the first wall portion 60 to the periphery of the second wall portion 61. The shape of the side wall portion 62 is frame shaped.

The first wall portion 60, the second wall portion 61 and the side wall portion 62 are integrated to form the tabletop body 43. In actual manufacturing of the tabletop body 43, the material such as a carbon composite material, for example, is extruded into a hollow cylindrical plate member, and openings at both ends of the plate member are sealed to thus manufacture the tabletop body 43.

As described above, the first wall portion 60 is formed in a manner that the first one end portion 60a has a smaller thickness than the portion other than the first one end portion 60a. Furthermore, the second wall portion 61 is also formed in a manner that the second one end portion 61a has a smaller thickness than the portion other than the second one end portion 61a. Thus, in the tabletop body 43, the X-ray transmission loss by the one end portion 43a in the longitudinal direction is smaller than the X-ray transmission loss by the portion other than the one end portion 43a.

As has been described above, according to the second embodiment of the present invention, the same effects as those of the first embodiment can be obtained. Additionally, since the cavity is formed inside the tabletop body 43, the tabletop body 43 achieves reduction in weight. Furthermore, since the tabletop body 43 can be manufactured by extruding the material such as a carbon composite material, the manufacturing of the tabletop body 43 can be facilitated.

Here, the interior space of the tabletop body 43 is filled with air. However, the filler is not limited to this. For example, the space may be filled with an air-containing material (for example, a foam material such as urethane foam). In this case, the strength of the tabletop body 43 can be improved in comparison with a case where the inside of the tabletop body 43 is cavity. It should be noted that if the X-ray transmission loss by the one end portion 43a is increased due to the filling with such a material, any one or both of the first one end portion 60a and the second one end portion 61a should be formed to have a smaller thickness so as to eliminate the increased amount in the loss.

According to at least one embodiment described above, the CT scanning tabletop 41 includes: the tabletop body 43 having the placement surface 43b where the subject P is placed, the tabletop body 43 formed in a manner that the X-ray transmission loss by the one end portion 43a in the longitudinal direction is smaller than the X-ray transmission loss by the portion other than the one end portion; and the aid 44 configured to hold a part of the subject P, the aid 44 provided on the one end portion 43a in a manner that the aid is attachable and detachable by moving in the advancing and retreating directions toward and away from the placement surface 43b. Thus, it becomes possible to make the X-ray transmission loss by the one end portion 43a and the aid 44 nearly as small as the loss by the portion other than the one end portion 43a, and also to reduce the work for attaching and detaching the aid 44.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A CT scanning tabletop, comprising:
a tabletop body having a placement surface where a subject is to be placed, the tabletop body being formed in a manner that an X-ray transmission loss by one end portion in a longitudinal direction thereof is smaller than an X-ray transmission loss by a portion of the tabletop body other than the one end portion; and
an aid provided on the one end portion in a manner that the aid is attachable and detachable by moving in advancing and retreating directions toward and away from the placement surface, the aid configured to hold a part of the subject,
wherein the tabletop body is formed in a manner that an X-ray transmission loss by the one end portion and the aid is nearly equal to that by the portion other than the one end portion.

2. The CT scanning tabletop according to claim 1, wherein the one end portion has such a thickness that the X-ray transmission loss by the one end portion and the aid is nearly equal to that by the portion other than the one end portion.

3. The CT scanning tabletop according to claim 1, wherein the aid is a headrest for holding a head of the subject placed in a lying posture on the tabletop body, and
the headrest is provided approximately at a center in a width direction of the tabletop body.

4. The CT scanning tabletop according to claim 1, wherein the aid includes:
a headrest provided approximately at a center in a width direction of the tabletop body and configured to hold a head of the subject placed in a lying posture on the tabletop body; and
an armrest provided on both sides of the headrest and configured to hold an arm of the subject, and
the armrest is provided on the one end portion in a manner that the armrest is attachable and detachable by moving in the advancing and retreating directions while the head of the subject is being held by the headrest.

5. The CT scanning tabletop according to claim 1, wherein the tabletop body is formed in a manner that the one end portion has a smaller thickness than the portion other than the one end portion.

6. A CT scanning tabletop, comprising:
a tabletop body having a placement surface where a subject is to be placed, the tabletop body being formed in a manner that an X-ray transmission loss by one end portion in a longitudinal direction thereof is smaller than an X-ray transmission loss by a portion of the tabletop body other than the one end portion; and
an aid provided on the one end portion in a manner that the aid is attachable and detachable by moving in advancing and retreating directions toward and away from the placement surface, the aid configured to hold a part of the subject, wherein
the tabletop body includes:
a first wall portion having the placement surface, and formed in a manner that a first one end portion in a longitudinal direction thereof has a smaller thickness than a portion of the first wall portion other than the first one end portion; and
a second wall portion facing the first wall portion at a distance, and formed in a manner that a second one end portion in a longitudinal direction thereof facing the first one end portion has a smaller thickness than a portion of the second wall portion other than the second one end portion.

7. A CT scanning tabletop, comprising:
a tabletop body having one end portion on which an aid is to be placed, the tabletop body being formed in a manner that an X-ray transmission loss by the one end portion in a longitudinal direction of the tabletop is smaller than an X-ray transmission loss by a portion of the tabletop other than the one end portion, wherein
the tabletop body is formed in a manner that an X-ray transmission loss by the one end portion and the aid is nearly equal to that by the portion other than the one end portion.

8. The CT scanning tabletop according to claim 7, wherein the one end portion has a smaller thickness than the portion other than the one end portion.

9. A CT scanning tabletop, comprising:
a tabletop body being formed in a manner that an X-ray transmission loss by one end portion in a longitudinal direction thereof is smaller than an X-ray transmission loss by a portion of the tabletop body other than the one end portion, wherein the tabletop body includes:
a first wall portion formed in a manner that a first one end portion in a longitudinal direction thereof has a smaller thickness than a portion of the first wall portion other than the first one end portion; and
a second wall portion facing the first wall portion at a distance, and being formed in a manner that a second one end portion in a longitudinal direction thereof facing the first one end portion has a smaller thickness than a portion of the second wall portion other than the second one end portion.

10. An X-ray CT apparatus, comprising:
a scanner configured to perform CT scanning of a subject;
a CT scanning tabletop on which the subject is to be placed; and
a bed configured to move the CT scanning tabletop toward the scanner, wherein the CT scanning tabletop includes:

a tabletop body having a placement surface where the subject is to be placed, and formed in a manner that an X-ray transmission loss by one end portion in a longitudinal direction thereof is smaller than an X-ray transmission loss by a portion of the table body other than the one end portion; and an aid provided on the one end portion in a manner that the aid is attachable and detachable by moving in advancing and retreating directions toward and away from the placement surface, the aid configured to hold a part of the subject, wherein the tabletop body is formed in a manner that an X-ray transmission loss by the one end portion and the aid is nearly equal to that by the portion other than the one end portion.

11. The X-ray CT apparatus according to claim 10, wherein the one end portion has such a thickness that an x-ray transmission loss by the one end portion and the aid is nearly equal to that by the portion other than the one end portion.

12. The X-ray CT apparatus according to claim 10, wherein the aid includes:
a headrest provided approximately at a center in a width direction of the tabletop body, and configured to hold a head of the subject placed in a lying posture on the tabletop body; and
an armrest provided on both sides of the headrest and configured to hold an arm of the subject, and
the armrest is provided on the one end portion in a manner that the armrest is attachable and detachable by moving in the advancing and retreating directions while the head of the subject is being held by the headrest.

13. The X-ray CT apparatus according to claim 10, wherein the tabletop body is formed in a manner that the one end portion has a smaller thickness than the portion other than the one end portion.

14. An X-ray CT apparatus, comprising:
a scanner configured to perform CT scanning of a subject;
a CT scanning tabletop on which the subject is to be placed; and
a bed configured to move the CT scanning tabletop toward the scanner, wherein the CT scanning tabletop includes
a tabletop body having a placement surface where the subject is to be placed, and formed in a manner that an X-ray transmission loss by one end portion in a longitudinal direction thereof is smaller than an X-ray transmission loss by a portion of the table body other than the one end portion; and
an aid provided on the one end portion in a manner that the aid is attachable and detachable by moving in advancing and retreating directions toward and away from the placement surface, the aid configured to hold a part of the subject, wherein the tabletop body includes:
a first wall portion having the placement surface, and being formed in a manner that a first one end portion in a longitudinal direction thereof has a smaller thickness than a portion of the first wall portion other than the first one end portion; and
a second wall portion facing the first wall portion at a distance, and being formed in a manner that a second one end portion in a longitudinal direction thereof facing the first one end portion has a smaller thickness than a portion of the second wall portion other than the second one end portion.

15. The CT scanning tabletop according to claim 6, wherein
an interior space of the tabletop body is filled with air; and
the second wall portion faces across a layer of air from the first wall portion.

16. The CT scanning tabletop according to claim 9, wherein
an interior space of the tabletop body is filled with air; and
the second wall portion faces across a layer of air from the first wall portion.

17. The X-ray CT apparatus according to claim 14, wherein
an interior space of the tabletop body is filled with air; and
the second wall portion faces across a layer of air from the first wall portion.

* * * * *